United States Patent [19]

Koetke

[11] Patent Number: 5,760,952
[45] Date of Patent: Jun. 2, 1998

[54] ILLUMINATING DEVICE FOR A SURGICAL MICROSCOPE

[75] Inventor: Jochen Koetke, Hamburg, Germany

[73] Assignee: J.D. Moller Optische Werke GmbH, Germany

[21] Appl. No.: 785,520

[22] Filed: Jan. 17, 1997

[30] Foreign Application Priority Data

Jan. 25, 1996 [DE] Germany ............ 296 01 263 U

[51] Int. Cl.$^6$ .................. G02B 21/06; A61B 3/10
[52] U.S. Cl. ............. 359/389; 359/385; 351/205; 351/221
[58] Field of Search .................. 359/368–369, 359/385–390; 351/205–206, 221, 243

[56] References Cited

U.S. PATENT DOCUMENTS

| | | | |
|---|---|---|---|
| 4,779,968 | 10/1988 | Sander | 359/389 |
| 4,932,774 | 6/1990 | Takagi et al. | 351/221 |
| 5,155,509 | 10/1992 | Kleinberg | 351/205 |
| 5,627,613 | 5/1997 | Kaneko | 351/205 |

FOREIGN PATENT DOCUMENTS

| | | |
|---|---|---|
| 595788 | 1/1994 | European Pat. Off. . |
| 4028605 | 3/1992 | Germany . |
| 4214445 | 11/1993 | Germany .................. 359/385 |
| 4331635 | 6/1994 | Germany .................. 359/385 |
| 4417273 | 11/1995 | Germany . |

*Primary Examiner*—Thong Nguyen
*Attorney, Agent, or Firm*—Murtha, Cullina, Richter & Pinney

[57] ABSTRACT

An illuminating device for a surgical microscope, which device has a light source arranged outside the observing beam path, a first deflector for light arranged between the light source and the observing beam path of the microscope, and a second deflector for light arranged closer to the observing beam path than the first deflector, is distinguished in that the first deflector comprises two deflecting elements of which one is fixed and the other is movable, and of which the deflecting element arranged closer to the observed object is also provided with a deflecting device on its side averted from the light source for directing light from the other deflecting element to the second deflector.

9 Claims, 7 Drawing Sheets

ILLUMINATING DEVICE FOR A SURGICAL MICROSCOPE

BACKGROUND OF THE INVENTION

The invention relates to an illuminating device for a surgical microscope, which device has a light source arranged outside the observing beam path, a first deflecting means for the light, which means is arranged between the light source and the observing beam path of the microscope, and further deflecting means for the light, which are arranged closer to the observing beam path than the first deflecting means.

Ophthalmic surgical operations place special demands on the illumination. The angle at which the eye is illuminated relative to the observing beam path of the surgeon is important. Good plasticity of the image by the formation of shadows on structures in the interior of the eye is achieved in the case of illumination of the eye at an angle of a few degrees, frequently at 6° to the observing beam path. If, by contrast, the eye is illuminated as coaxially as possible relative to the observing beam path (that is to say, the angle between the observing beam path and illuminating beam path is as small as possible), this leads to the formation of the so-called red reflex. The pupil of the operated eye is lit up in a reddish fashion by the light backscattered from the retina. This type of illumination is very advantageous in cataract operations, because tissue remnants which occur upon removal of the lens and are to be removed without fail to prevent complications can be effectively detected in the backlighting of the red reflex. The generation of the red reflex has become an important aid in modern operating techniques.

In addition to the red-reflex illumination, the simultaneous illumination at about 6° is advantageous, because the abovementioned plasticity of the image cannot be achieved at the small angles required for generating the red reflex. However, a red reflex is not desired in all stages of the operation. An optimum illumination module must therefore offer two illumination settings: in the first position, the OP field is illuminated by a combination of the 6° illumination and the more coaxial illumination relative to the generation of the red reflex. Only illumination at 6° is performed in the second position.

In a known illuminating device of the type mentioned at the beginning (DE 40 28 605 A1), the light falls onto a mirror inclined at 45°, which is arranged outside the observing beam path of the microscope, and is deflected there onto the object, with the result that the deflected light beam impinges on the object at an angle of about 6°. This mirror is provided with a cutout through which light impinges on a second mirror, which is arranged close to the observing beam path or on the same. The second mirror is displaceable, with the result that the angle between the direction of illumination and the observing beam path can be set to values between approximately 0° and 4°. The intensities of illumination of the two beam paths can be set by diaphragms in the case of the two mirrors. A disadvantage of this arrangement is that the red reflex produced is inhomogeneous, and this impairs the visualization of tissue remnants. The inhomogeneity is conditioned by the arrangement of the mirror for generating the red reflex, which arrangement is asymmetric relative to the observing beam paths. In the abovementioned prior art, this mirror is arranged between the two observing beam paths.

In some other microscopes, the patient's eye is therefore illuminated absolutely coaxially relative to the observing beam path via beam splitter plates for the purpose of a uniform red reflex. Since the surgeon must look through these plates, only a low intensity of illumination is possible, however, with the result that the intensity of the red reflex is low.

SUMMARY OF THE INVENTION

It may be said in summary that, for the purpose of a uniform intensive red reflex, the eye must be illuminated as coaxially as possible relative to the illuminating beam path. Furthermore, for the purpose of good homogeneity of the red reflex the illuminating optics (mirrors, prisms, etc.) must be arranged as symmetrically as possible relative to the observing beam paths. The illuminating module must, moreover, offer the surgeon the possibility of selecting between the two types of illumination outlined above by switching.

The object of the invention is therefore to provide a surgical microscope which avoids the said disadvantages and permits more effective work with the microscope.

By contrast with the prior art, it is not the further deflecting means which are displaceable, but the first deflecting means or a part of the first deflecting means. As a result, the further deflecting means can be arranged close to the observing beam paths, and surrounding the same completely or partly. A very uniform red reflex is thereby obtained. The setting of the relative brightnesses between a 0° illumination (what is meant here is the illumination for the red reflex, which can also have a small angle different from 0°) and a 6° illumination can be selected in the desired way.

The light for the 0° illumination is directed from a deflecting element of the first deflecting means onto the other and then guided from the rear thereof to the further deflecting means for the 0° illumination. In an alternative embodiment, the deflecting element, which is further removed from the observed object, of the first deflecting means is arranged displaceably, as a result of which a similar effect can be obtained. It is in this case essentially only the angular range which can be achieved with the 6° illumination which changes.

Since the further deflecting means are arranged not only between the two observing beam paths, but also on both sides of the same, the further deflecting means must be illuminated over a relatively large area. This can lead to space problems because of the compact design of the microscopes. It is therefore advantageous to provide additional deflecting elements between the first deflecting means and the further deflecting means. The original light beam and the first deflecting means can therefore be constructed to be relatively small, the light beams for the 0° illumination then being fanned out behind the first deflecting means by the additional deflecting elements and being directed onto the various deflecting elements of the further deflecting means.

Normally, one deflecting element of the further deflecting means will be provided in each case between the two observing beam paths and on the outside of these beam paths. The further deflecting means can, however, also be in one piece and surround the two beam paths, for example a mirror with two bores for the observing beam paths.

In order to vary the brightness of the 6° illumination (of course, the angle of this lateral illumination need not be precisely 6°), it is possible in addition to the fact that one deflecting element of the first deflecting means is displaceable, to provide a diaphragm in the beam path of the first deflecting means.

The illuminating device can have one or more light sources. Prisms can be used as deflecting means. In a particularly expedient embodiment, the deflecting means are, by contrast, mirrors.

BRIEF DESCRIPTION OF THE DRAWING

The invention is described below by way of example with the aid of advantageous embodiments with reference to the attached drawings, in which.

DESCRIPTION OF THE PREFERRED EMBODIMENTS

Figure 1:
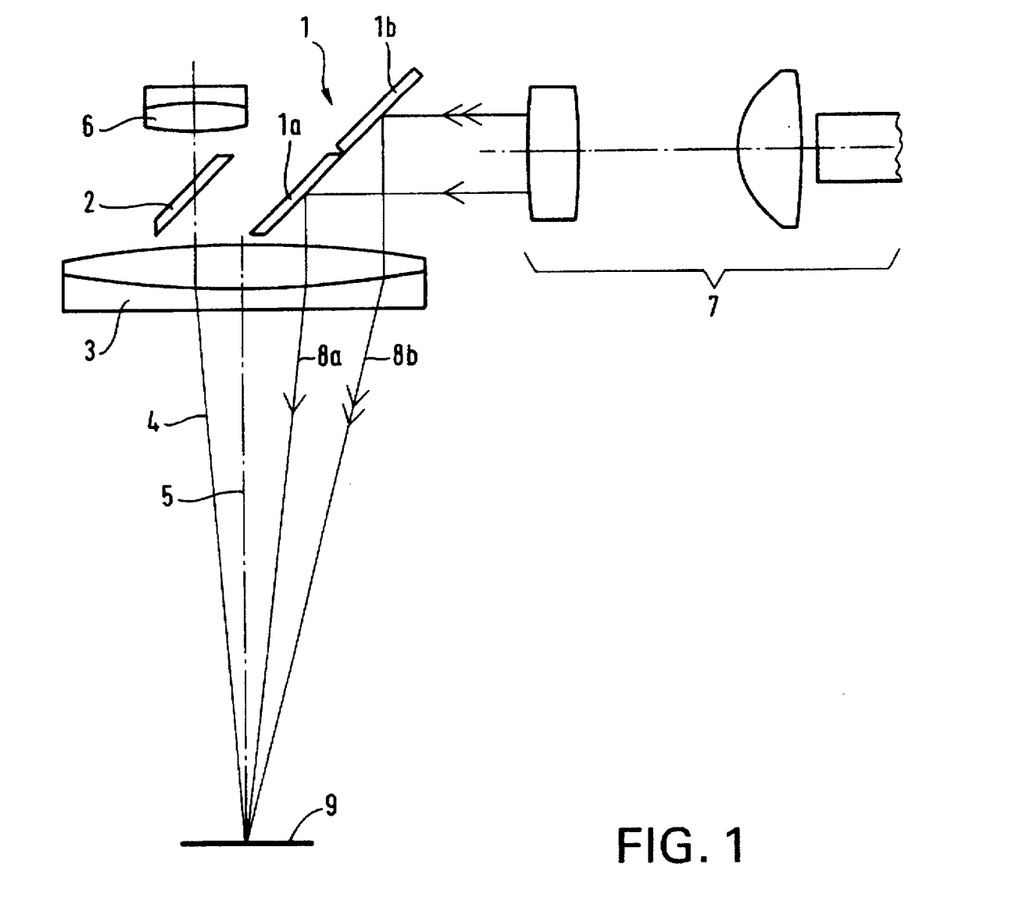
FIG. 1 shows a side view of the beam path in a diagrammatic form for one embodiment.
Figure 2:
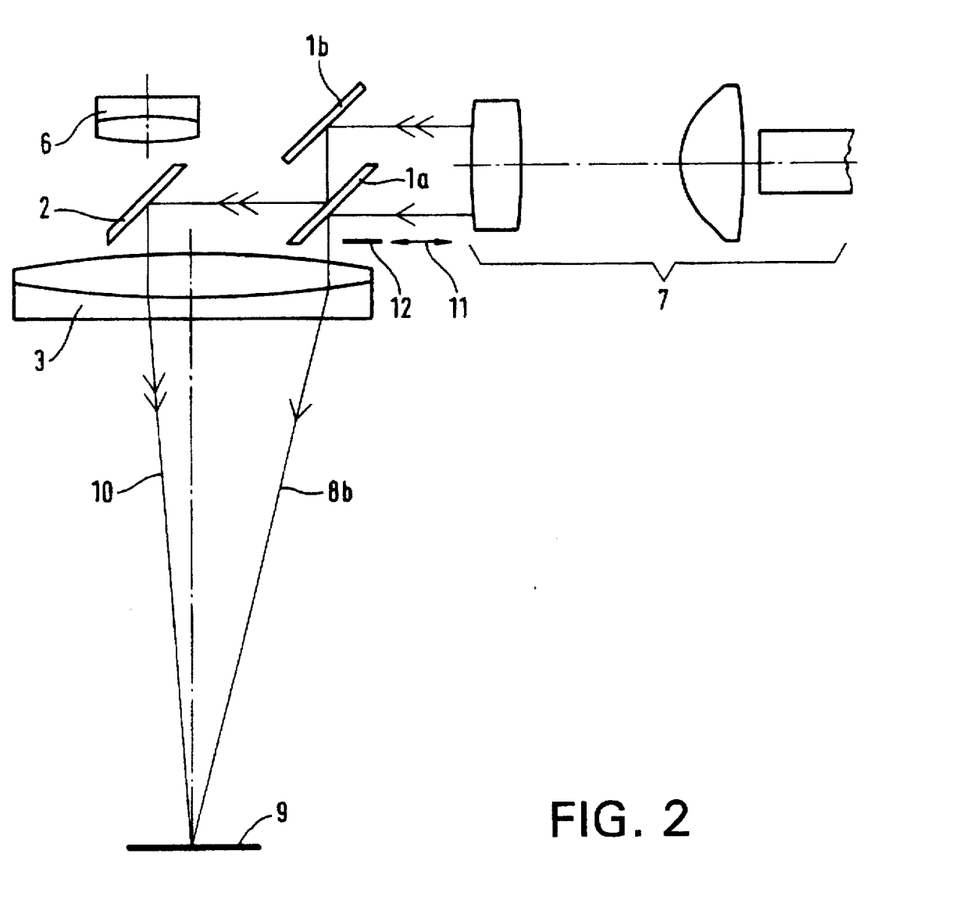
FIG. 2 shows the beam path of the embodiment of FIG. 1 in another operating position.

The objective of a surgical microscope is denoted by 3 in the figures (reference being made first to FIGS. 1 and 2). The observing beam path 4 extends a little outside the optical axis 5. The observing beam path 4 in this case passes through further lenses 6. Since the presentation is from the side, only one of the two observing beam paths 4 of the stereomicroscope can be seen; the other is situated behind the observing beam path shown.

Figure 2A:
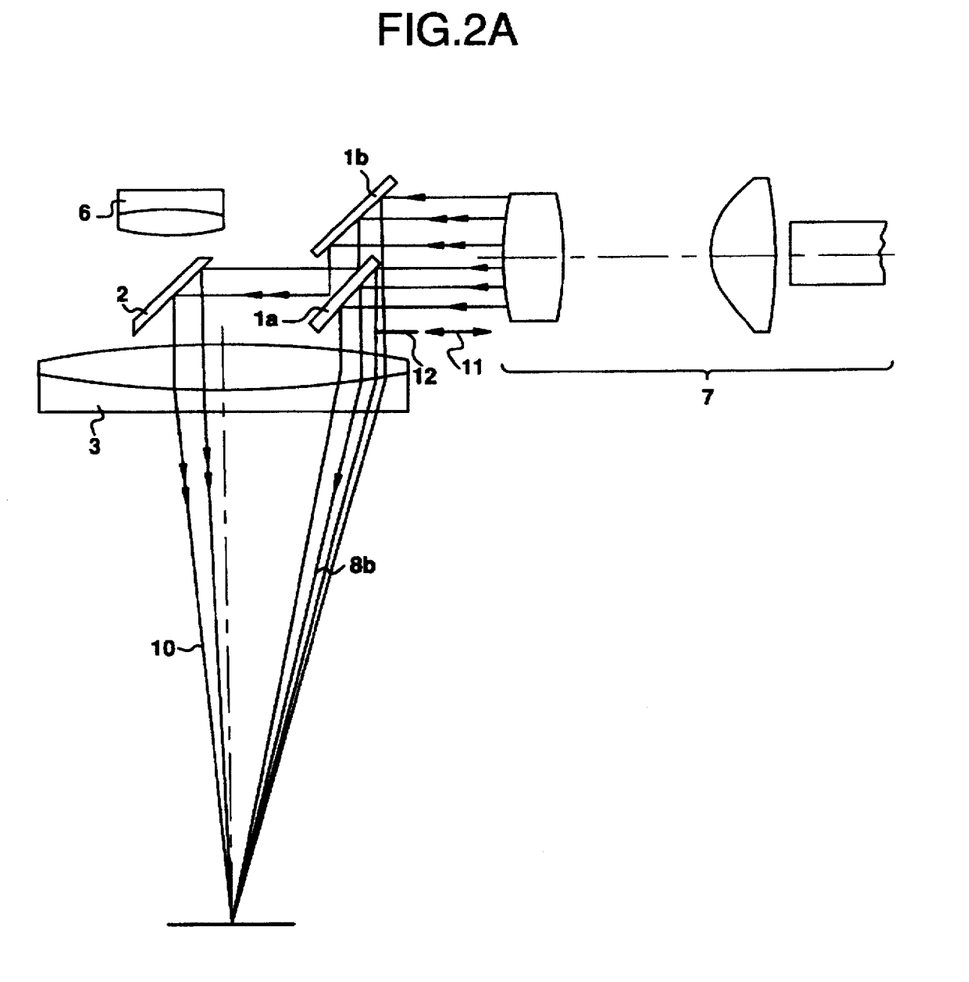
FIG. 2A shows the beam path of the embodiment of FIG. 2 in a different operating position.

Shown on the right in FIGS. 1, 2, 2A, 4, 7 and 7A is an illuminating device 7 which directs light onto a first deflecting means 1 which comprises two mirrors 1a, 1b. These mirrors 1a and 1b direct the light onto the object 9 in the form of light bundles 8a, 8b at an average angle of approximately 6°. In the position shown in FIGS. 2 and 2A, the mirror 1a positioned close to the object 9 has been moved in the direction of the light source 7 and now generates a light bundle which corresponds to the light bundle 8b in FIG. 1 and effects the 6° illumination. The light falling onto the mirror 1b is deflected onto the rear of the mirror 1a and from there onto the further deflecting means 2, and is then directed onto the object 9 as a near-axis light bundle 10 (0° illumination). As shown in FIGS. 2 and 2A, the relative intensity of the two light bundles 8b and 10 can be controlled, on the one hand, by displacing the mirror 1a in the direction of the double arrow 11 and, on the other hand, by a displaceable diaphragm or light shield 12 by means of which the light bundle 8b can be partially dimmed.

Figure 3:
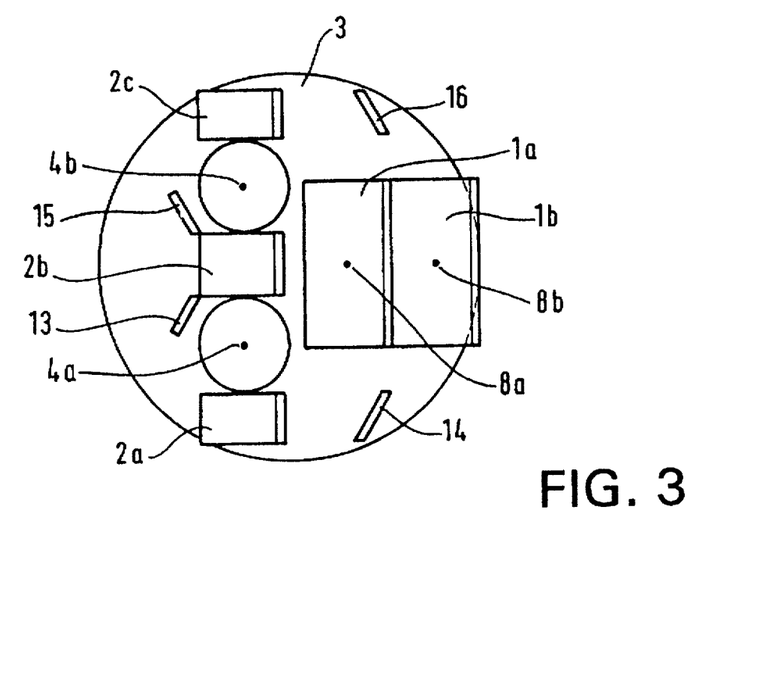
FIG. 3 shows a top view of the optical elements in the position of FIG. 1.
Figure 4:
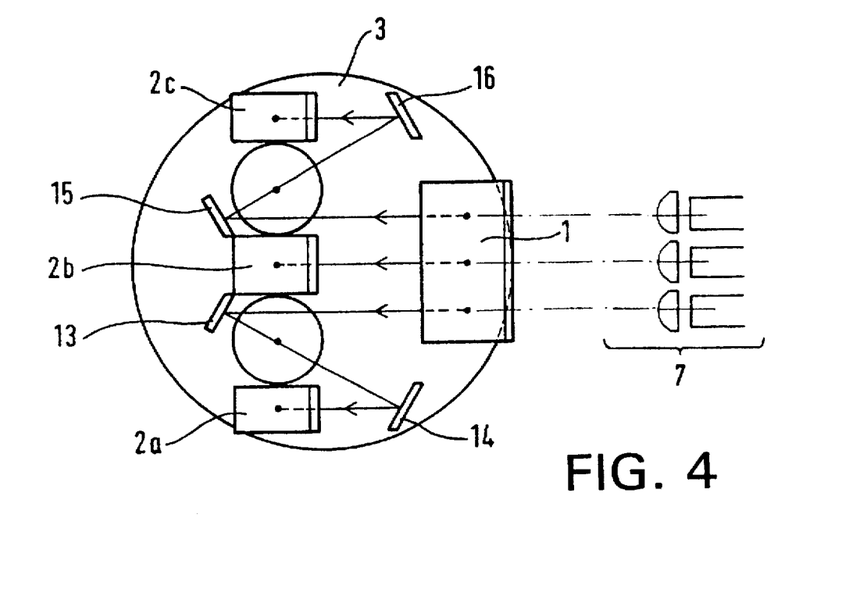
FIG. 4 shows a top view of the optical elements in the position of FIG. 2.

As is to be seen from FIG. 3, the further deflecting means 2 comprise three mirrors 2a, 2b, 2c, which are arranged on both sides of the observing beam paths 4a, 4b. In the position in FIG. 4, the light is directed onto the central mirror 2b directly by the mirrors 1a, 1b, while it is directed onto the two outer mirrors 2a, 2c via additional deflecting mirrors 13 to 16.

Figure 5:
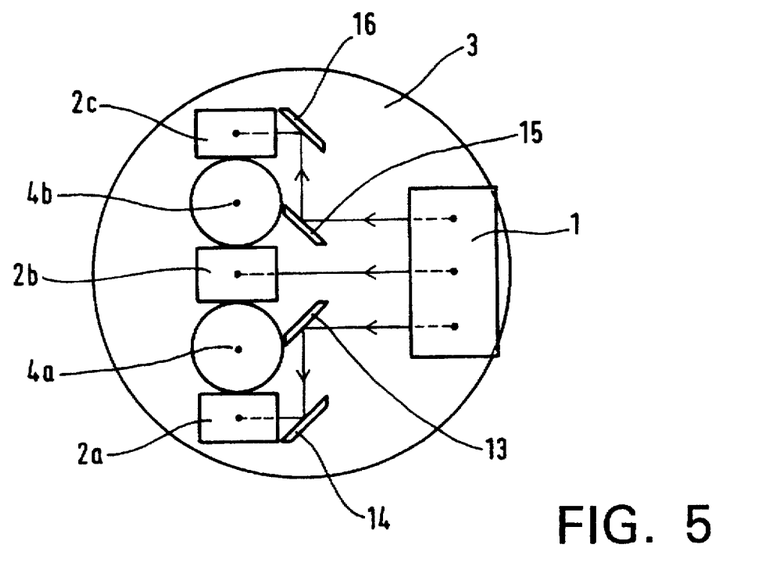
FIGS. 5 and 6 show alternative embodiments in top views of the optical elements.

In the embodiment in FIG. 5, the additional mirrors 13 to 16 are positioned otherwise. By contrast with that in FIGS. 3 and 4, this embodiment is less complicated, but can fail in practice for reasons of space, because the mirrors 13 and 15 are now arranged between the observing beam paths 4a and 4b and the mirror 1a.

Figure 6:
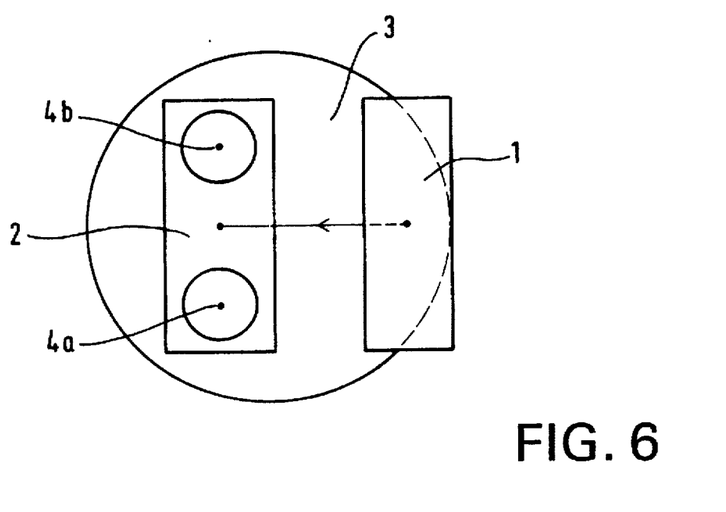

In the embodiment in FIG. 6, the mirror 2, which is constructed in one piece, surrounds the observing beam paths 4a and 4b and is provided for this purpose with bores through which the observing beam paths pass.

All these embodiments permit the relative intensity of illumination for the red reflex and the 6° illumination which increases the plasticity to be varied in order to obtain optimum operating conditions.

The greatest possible quantity of light of 50% of the entire quantity of light can be directed, for the purpose of generating the red reflex, onto the deflecting elements 2a to 2c given an area ratio of 1:1 for the mirrors 1a and 1b. The intensity of illumination for generating the red reflex can be dosed continuously by moving the mirror 1a, with the result that it is possible to set a ratio of the intensity of the beams which is individually preferred by the surgeon.

The three mirrors 2a, 2b and 2c are arranged with maximum symmetry relative to the observing beam paths 4a, 4b, so that the red reflex lights up for the observer as homogeneously as possible over the entire pupil area. Each of the two observing beam paths 4a, 4b is flanked, for this purpose, by in each case two mirror elements 2a, 2b or 2c. With the mirror arrangement according to the invention, the quality of light coming from the mirror 1a is utilized completely to generate the red reflex, that is to say it is thus possible to use the high intensity of 50% of the light of the light source to generate the red reflex.

Figure 7:
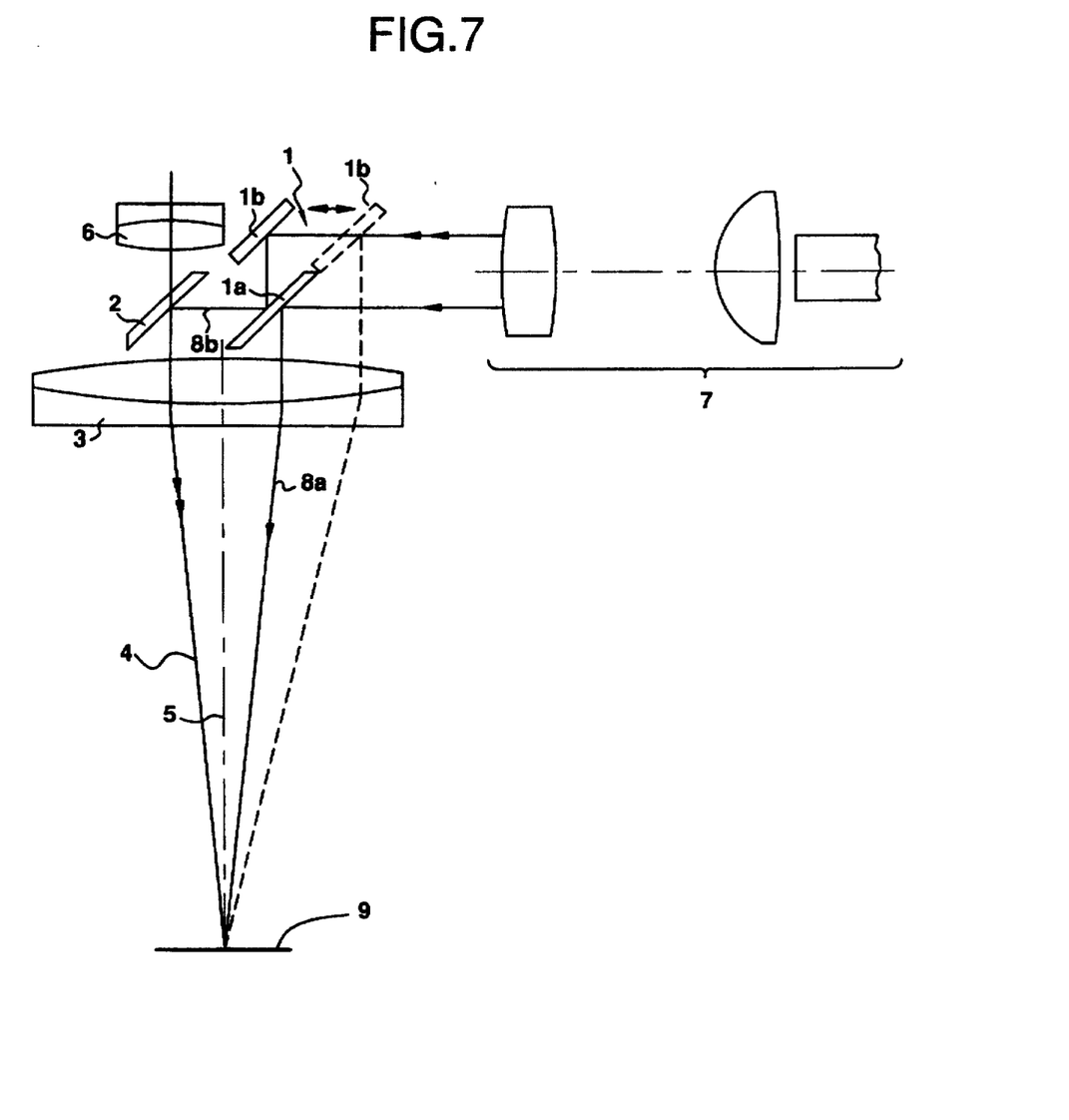
FIGS. 7 and 7A show further alternative embodiments in a side view of the optical elements.

As shown in FIG. 7, a similar function would be obtained if in the case of the arrangement in FIG. 1 the mirror part 1a were mounted in a fixed fashion and the mirror part 1b were displaced at right angles to the observing beam path. Accordingly, the deflecting element 1b which is disposed further from the observed object 9, with respect to the position of the first deflecting element 1a, is movable toward and away from the light source 7. The consequence of this solution would be that the fixed mirror 1a near the observing beam paths contributes, in additional to the mirrors 2a, 2b, 2c, to the generation of the red reflex. However, the plasticity of the image would be reduced simultaneously.

Figure 7A:
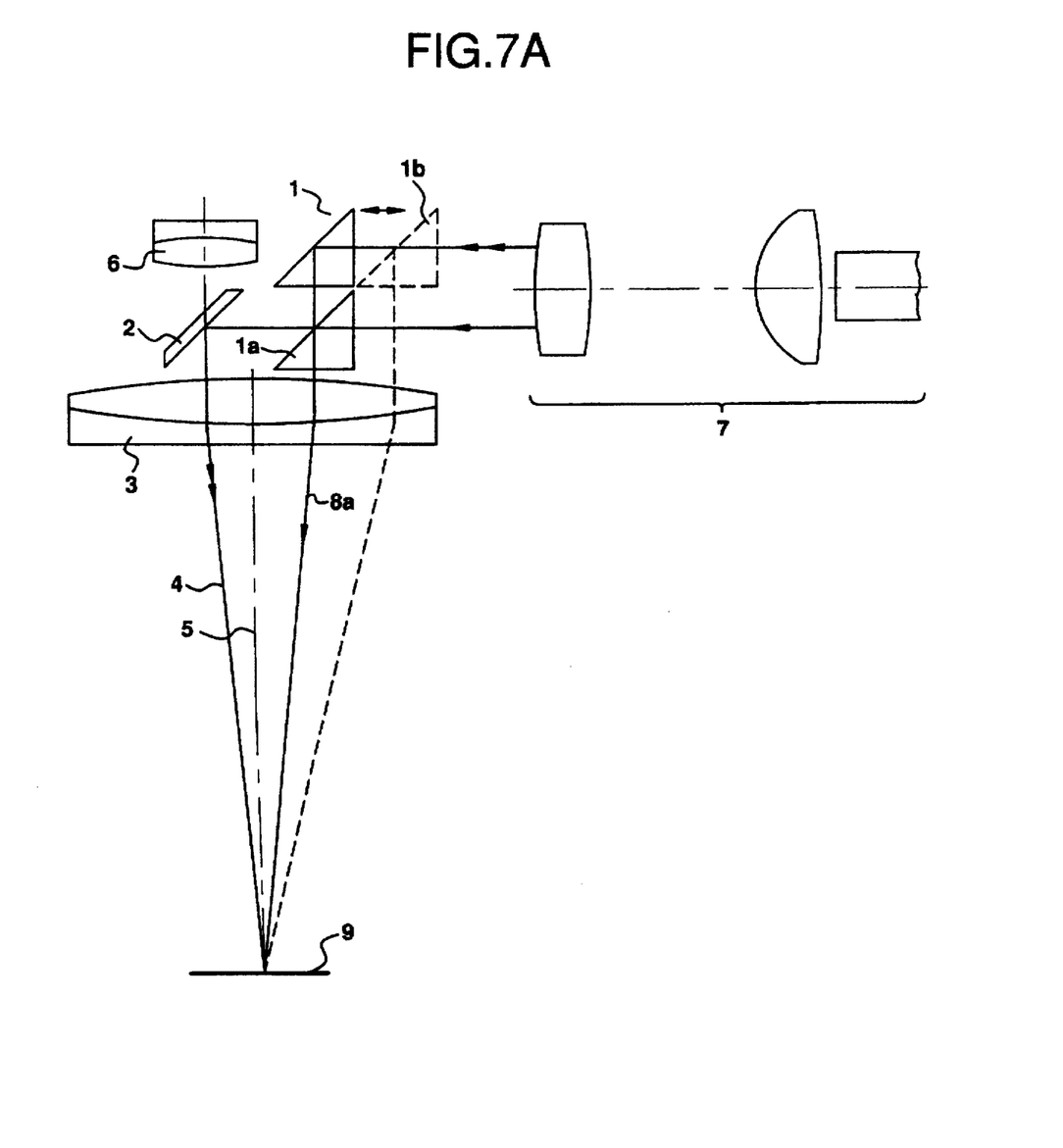

An alternative embodiment similar to FIG. 7 is shown at FIG. 7A wherein prisms 1a and 1b are provided as deflecting elements of deflecting means 1.

I claim:

1. In combination with an illuminating device for a surgical microscope having a light source arranged outside an observing beam path, a first deflecting means for light disposed between the light source and the observing beam path of the microscope, and a second deflecting means for light disposed closer to the observing beam path than the first deflecting means, the improvement which comprises:

the first deflecting means including two deflecting elements of which one is movable, the deflecting element disposed closer to an observed object having a deflecting device on its side averted from the light source for directing at least part of the light, from the deflecting element disposed further from the observed object, to the second deflecting means.

2. Surgical microscope according to claim 1 wherein further deflecting elements are provided between the first and the second deflecting means.

3. Surgical microscope according to claim 1 further including a second observing beam path, and wherein the second deflecting means is in one piece and surrounds the observing beam paths.

4. Surgical microscope according to claim 1 wherein the deflecting element disposed closer to the observed object is movable toward and away from the light source.

5. Surgical microscope according to claim 1 wherein the deflecting element disposed further from the observed object, with respect to the position of the first deflecting element is movable toward and away from the light source.

6. Surgical microscope according to claim 1 wherein a light shield is disposed in the beam path between the first deflecting means and the observed object.

7. Surgical microscope according to claim 1 wherein a plurality of light sources is provided.

8. Surgical microscope according to claim 1 wherein prisms are provided as deflecting means.

9. Surgical microscope according to claim 1 wherein mirrors are provided as deflecting means.

* * * * *